United States Patent [19]

Shoberg et al.

[11] Patent Number: 5,584,873
[45] Date of Patent: Dec. 17, 1996

[54] MEDICAL LEAD WITH COMPRESSION LUMENS

[75] Inventors: Bret R. Shoberg, Corcoran; Svenn E. Borgersen, Eagan; Michael R. Dollimer, Oakdale, all of Minn.

[73] Assignee: Medtronic, Inc., Minneapolis, Minn.

[21] Appl. No.: 438,125

[22] Filed: May 8, 1995

[51] Int. Cl.[6] .................................................... A61N 1/05
[52] U.S. Cl. ........................................... 607/122; 128/642
[58] Field of Search ..................... 607/116, 119, 607/122–128; 128/642; 604/282; 600/128, 138

[56] References Cited

U.S. PATENT DOCUMENTS

| | | | |
|---|---|---|---|
| 4,608,986 | 9/1986 | Beranek et al. | 607/123 |
| 5,324,321 | 6/1994 | Pohndorf et al. | 607/116 |
| 5,358,517 | 10/1994 | Pohndorf et al. | 607/116 |
| 5,458,629 | 10/1995 | Baudino et al. | 607/116 |
| 5,466,253 | 11/1995 | Doan | 607/122 |

*Primary Examiner*—Jeffrey R. Jastrzab
*Attorney, Agent, or Firm*—Reed A. Duthler; Harold R. Patton

[57] ABSTRACT

A medical electrical lead having a multiple conductors located within an elongated lead body which is provided with multiple conductor lumens each containing a conductor and with at least one compression lumen which does not contain a conductor. The conductor lumens are spaced from one another by a first, minimum spacing and the compression lumen or lumens are located intermediate the conductor lumens and are spaced from the conductor lumens by a second, minimal spacing of less then said first minimum spacing. The centers of the compression lumens are located along lines which pass through the both the center of a conductor lumen and the center of the lead body. The arrangement of the conductor and compression lumens enhances the lead's ability to survive crushing forces such as applied by the first rib and clavicle.

14 Claims, 2 Drawing Sheets

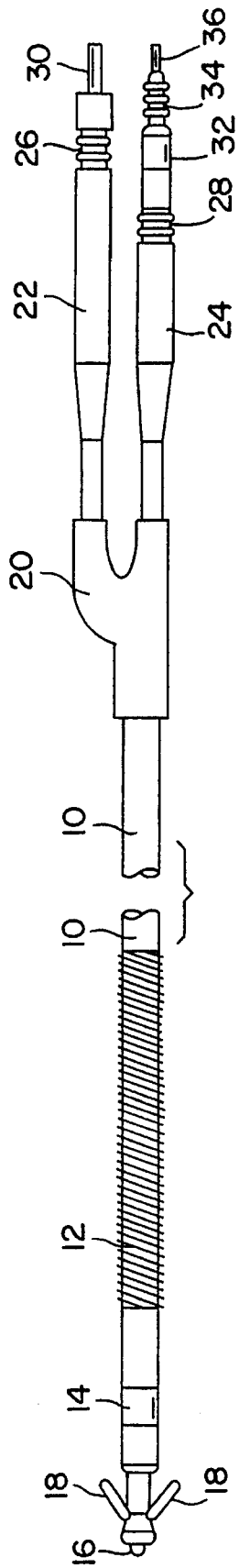
FIG. 1
PRIOR ART
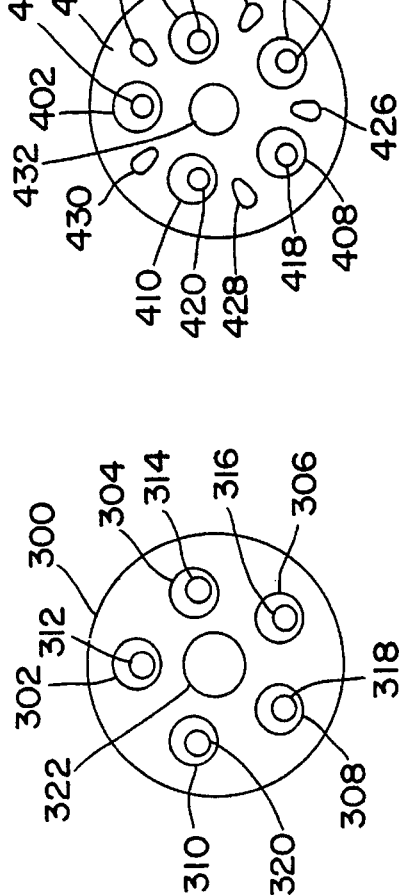
FIG. 5
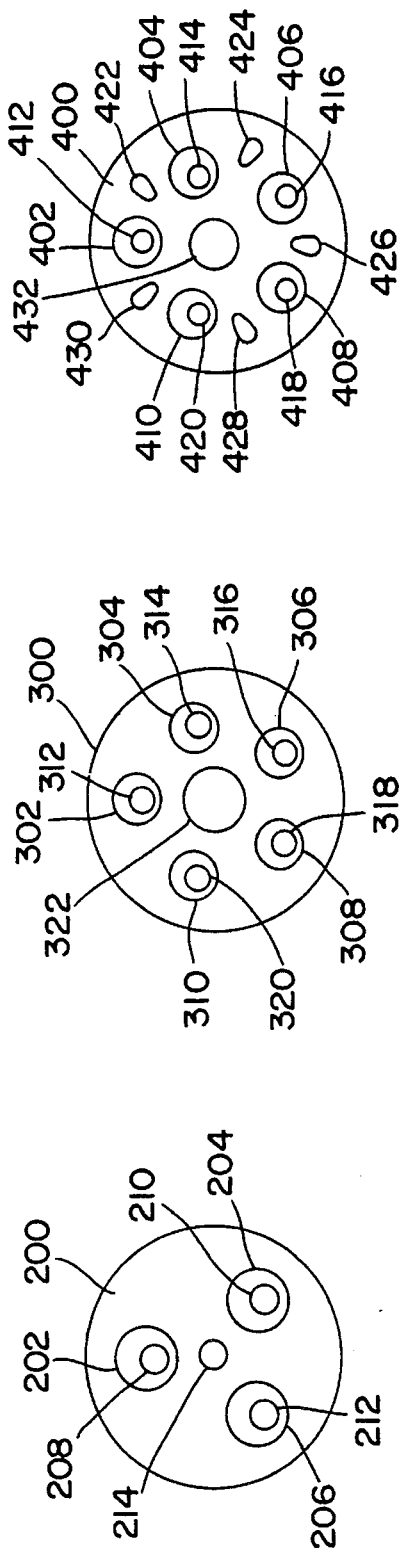
FIG. 4
FIG. 3

MEDICAL LEAD WITH COMPRESSION LUMENS

BACKGROUND OF THE INVENTION

The present invention relates to implantable medical electrical leads, and more particularly relates to multi-lumen, multi-conductor leads.

In the context of implantable electrical leads, such as those employed in conjunction with implantable pacemakers, implantable nerve stimulators, and implantable cardioverter/defibrillators, it has become clear that leads which are passed between adjacent bony structures within the body have the potential to be damaged due to crushing between these bony structures. A simple mechanism for increasing the resistance of an electrical lead to damage due to crushing is to simply decrease the diameter of the lead body. However, this approach must be balanced with the requirement that the lead body must be large enough to provide room for all conductors and the requirement that the lead remain flexible enough to yield compliantly under crushing forces. One known approach to reduce the diameter is to substitute non-helical conductor for the coiled conductors typically used in implantable leads. For example, having non-helical conductors are disclosed in U.S. Pat. No. 5,324,321 issued to Pohndorf et al and U.S. Pat. No. 4,608,986 issued to Beranek.

SUMMARY OF THE INVENTION

The present invention also addresses the problem of providing for crush resistance in the context of an implantable medical lead. In the context of the present invention, additional lumens which do not carry conductors are provided specifically to enhance the ability of the lead to compress without creating excessive stresses within the polymeric lead body. These lumens (hereafter "compression lumens") are preferably located between intermediate lumens carrying conductors (hereafter "conductor lumens"), such that the centers of the compression lumens are each located along a diameter passing through the center of the lead body and through the center of a corresponding conductor lumen. Finite element analysis testing performed by the inventors have verified that the provision of these compression lumens provides for a substantial benefit in producing a lead with an enhanced ability to survive crushing forces, applied across the lead, as would occur when the lead is compressed between bony structures within the body.

Generally, the preferred embodiment of the invention takes the form of a lead having a lead body formed of an elongated extruded multi-lumen tube, with the conductor lumens and compression lumens running in parallel, along the length of the tube. Preferably, the compression lumens have as great a dimension measured radially as is possible, consistent with the requirement of maintaining a minimum spacing or wall thickness between the compression lumens and adjacent conductor lumens. Preferably, the minimum spacing or minimum wall thickness between adjacent conductor lumens is greater than the minimum spacing or minimum wall thickness between a conductor lumen and a immediately adjacent compression lumen. By this arrangement, in the event that a fracture of the lead body occurs as a result of compression of the lead, it will occur between a conductor lumen and an adjacent compression lumen, rather than between adjacent conductor lumens, which could result in a short between the conductors located therein.

In some embodiments of the preferred invention, conductor lumens and compression lumens are arranged alternate to one another, around the circumference of the lead body. In other embodiments, a plurality of conductor lumens are arranged around the circumference of lead, with a compression lumen or lumens located centrally. The benefit of the compression lumens is provided whether the conductors take either the form of traditional, coiled conductors, or the form of non-helical conductors, such as bundled stranded wires.

Brief Description of the Drawings

FIG. 1 is a plan view of a Prior Art implantable lead of the type in which the present invention may be practiced.

FIG. 3 is cross-sectional view through a lead body according to the present invention, illustrating a second preferred relationship between conductor lumens and a centrally located compression lumen.

FIG. 4 is a cross-sectional through a lead body according to the present invention, illustrating a third preferred relationship between conductor lumens and a centrally located compression lumen.

FIG. 5 is a cross-sectional view through a lead body according to the present invention, illustrating a fourth preferred relationship between conductor lumens and a peripherally located compression lumens.

Detailed Description of the Preferred Embodiments

Figure 2:
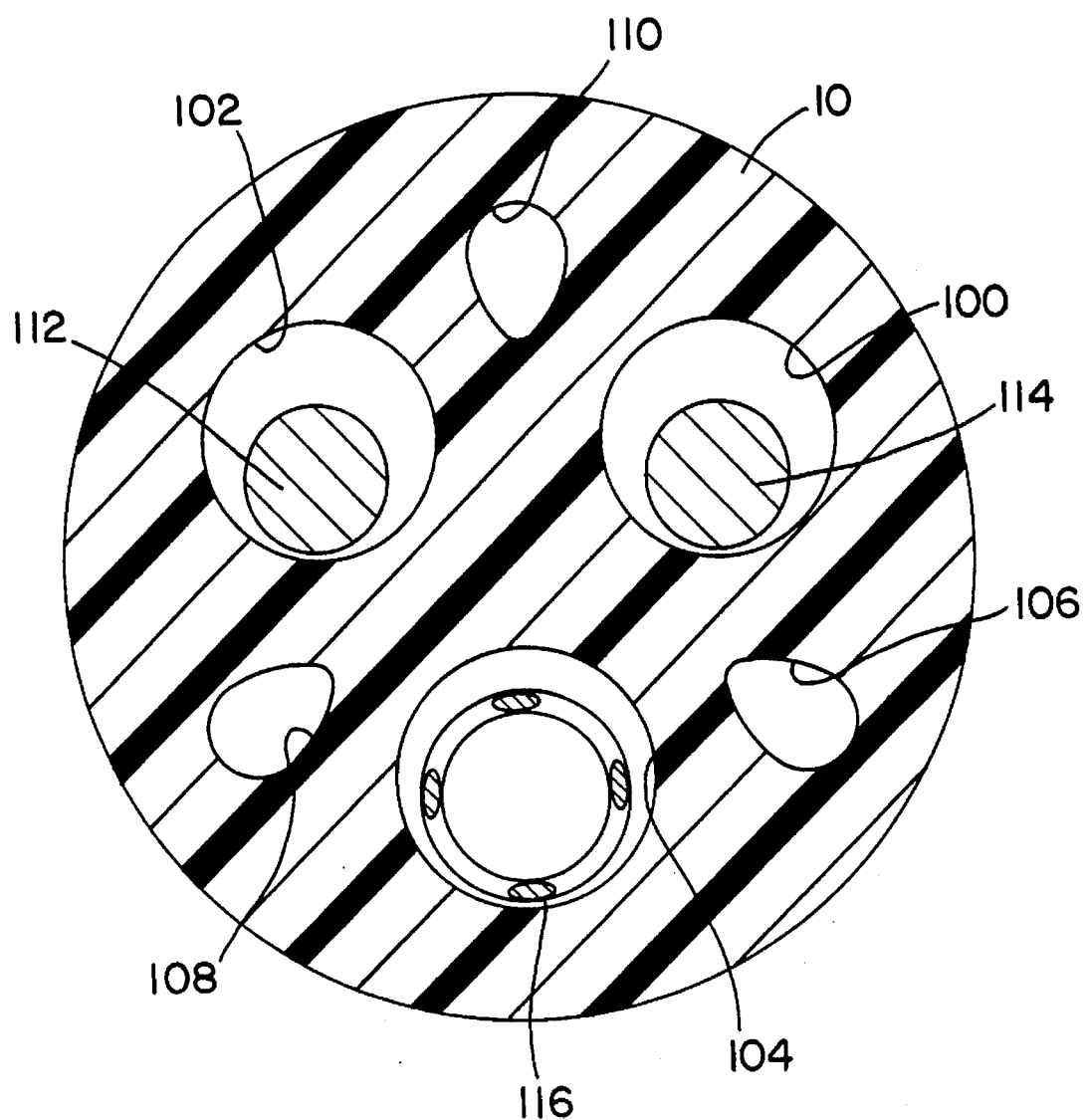
FIG. 2 is cross-sectional view through the lead of FIG. 1, illustrating a first preferred relationship between the conductor lumens and the compression lumens in a first embodiment of the invention.

FIG. 1 is a plan view of a defibrillation lead of the type in which the present invention may usefully be practiced. The present invention, of course, may also be usefully practiced in the context of other medical electrical leads, such as cardiac pacing leads, nerve and muscle stimulation leads, and so forth.

The lead of FIG. 1 is provided with an elongated insulative lead body 10, preferably fabricated of silicone rubber, polyurethane or other biocompatible elastomer. At the proximal end of the lead, it carries an elongated defibrillation 12, a ring electrode 14 and a tip electrode 16, each coupled to a conductor located within the lead body 10. Tines 18 are provided in maintaining electrode 16 in contact with the tissue of the right ventricle. Electrodes 16, 14 and 12 may correspond to any conventionally available pacing and defibrillation electrodes.

The proximal end of the lead carries a connector assembly, beginning with a molded lead bifurcation 20, which splits off two of the conductors within lead body 10 to a bipolar, in-line connector assembly 24, generally corresponding to the IS-1 connector standard for pacing leads. Connector assembly 24 is provided with a first set of sealing rings 28, a connector ring 32, a second sealing rings 34 and connector pin 36. Connector pin 36 is coupled to the conductor which extends through the lead body 10 to tip electrode 16. Connector ring is coupled to the conductor which extends through the lead body 10 to ring electrode 14. The conductor coupled to defibrillation electrode 12 extends into connector assembly 22, which carries a set of sealing rings 26 and a connector pin 36, coupled to the conductor extending through lead body 10 to defibrillation electrode 12. The illustrated connector assemblies are conventional elements, and may correspond to any of the numerous known electrical connector assemblies provided on implantable medical leads.

Although not visible in FIG. 1, it should be noted that the elongated conductors passing through lead body 10 may be any of the various known available conductors for use in conjunction with implantable electrical leads, including monofilar or multifilar coiled conductors, bundled stranded conductors, and the like. In the specific context of the lead illustrated in FIG. 1, the connector coupling connector pin 32 to electrode 16 takes the form of a multifilar coiled conductor to allow passage of a stylet therethrough, while the conductors coupling ring electrode 14 to connector ring 32 and coupling defibrillation electrode 12 to connector pin 30 take the form of bundled, stranded wires, provided with a coating of PTFE. However, the present invention is believed workable in the context of any of the numerous conductors known for use in implantable electrical leads, in any combination with one another.

FIG. 2 illustrates a cross-section through lead body 10, illustrating the inter-relation of the conductor lumens 100, 102 and 104 with the compression lumens 106, 108 and 110. In this view it can be seen that the conductor lumens contain three conductors, comprising conductors 112 and 114 which take the form of TEFLON coated bundled stranded wires having a generally straight configuration and a more conventional multifilar coiled conductor 116.

In this view, it can be seen that the minimum wall thickness separating the conductor lumens 100, 102 and 104 from one another is thicker than the minimum wall thickness separating the compression lumens 106, 108 and 110 from the most closely adjacent conductor lumens. It should also be noted that each of the compression lumens 106, 108 and 110 has its center located along a diameter through lead body 10, which passes through the center of a corresponding one of the conductor lumens. For example, compression lumen 110 has it center located along a diameter passing through the center of lead body 10 and through the center of conductor lumen 104. This arrangement is believed beneficial in assisting the lead in resisting crushing forces, applied by the first rib and clavicle, across the lead the body. Conductor lumen 102 and compression lumen 106, as well as conductor lumen 100 and compression lumen 108 are correspondingly arranged.

In this view, it can also be seen that compression lumens 106, 108 and 110 display an elongated, tear drop shape in cross-section. In the context of the present invention, the inventors have determined that it is desirable, in order to assist the ability of the lead to resist damage due to crushing, that the compression lumens have as great a radial extent as is possible, consistent with provision of a desired minimum wall thickness between the compression lumens and adjacent conductor lumens. The inventors have also determined that it is desirable that the compression lumens display a convex configuration such as a circle, oval or egg-shaped configuration, rather than a cross-section which includes concave, inwardly directed curved wall portions. The combined effect of these two considerations, in the context of the embodiment illustrated in FIG. 2 results in the provision of the generally egg-shaped, elongated lumen cross-sections illustrated. In the context of other embodiments, however, oval, circular or other lumen configurations might be the most desirable.

While the specific minimum wall thicknesses separating adjacent conductor lumens from one another and separating compression lumens from adjacent conductor lumens will vary as a function of the specific material chosen, in the context of the actual embodiment developed by the inventors, intended for commercial use, employing a silicone rubber lead body, workable dimensions are set forth below.

Lead body 10 has a diameter of 0.102 inches (2.59 millimeters). Conductor lumens 100, 102 and 104 have diameters of 0.029 inches (0.736 millimeters) respectively, and are spaced from one another by a minimum wall thickness of 0.010 inches (0.254 millimeters). Compression lumens 106, 108 and 110 have a maximum length measured along a radius through the center of lead body 10 of 0.020 inches (0.508 millimeters), and a maximum width measured perpendicular to the radius of the lead body 10 of 0.014 inches (0.356 millimeters). The minimum wall thickness separating the interior of conductor lumens 100, 102 and 104 from the exterior of lead body 10 is 0.012 inches (0.305 millimeters). The minimum wall thickness separating compression lumens 106, 108 and 110 from the exterior lead body 10 is 0.009 inches (0.229 millimeters). Conductors 112 and 114 take the form of bundled stranded wires fabricated of silver cored MP35N wire, including 49 filars, coated with an extruded coating of PTFE, and having an overall diameter of 0.017 inches (0.432 millimeters) Conductor coil 16 takes the form of a multifilar coil of five MP35N wires, wound to display an overall diameter of 0.026 inches (0.660 millimeters), and having an internal lumen of 0.018 inches (0.457 millimeters), in order to allow passage of a stylet therethrough.

Finite element analysis (FEA) studies performed by the inventors indicate that a design as illustrated in FIG. 2 provides a lead body which is highly compliant and is capable of withstanding significant crushing forces without creating excessive stresses in the polymer of the lead body. This characteristic, in turn, is believed to decrease the probability that crushing forces applied to the lead body will cause the conductors to break through the through the lumen walls or outer surface of the lead body and to correspondingly enhance the ability of the lead body to withstand multiple applications of crushing force.

FIGS. 3–5 illustrate alternative embodiments of lead bodies employing compression lumens. The drawings are not intended to be scale, but to illustrate basic configurational considerations associated with providing compression lumens to assist in complying to compressive forces applied across the lead body.

FIG. 3 shows a lead body 200 which contains three conductor lumens 202, 204 and 206, each containing a respective conductor 208, 210 and 212. In this embodiment, a single compression lumen 214 is provided located centrally within the lead body. In this view, it can be seen that the minimum wall thickness separating the conductor lumens, 202, 204 and 206 from one another is greater than the minimum wall thickness separating the conductor lumens from compression lumen 214. It can be seen that the compression lumen 214 has its center located at their center of the lead body and thus along a diameter passing through the center of each of the conductor lumens 202, 204 and 208.

FIG. 4 illustrates a variant of the configuration illustrated in FIG. 3, in which the lead body 300 is provided with five conductor lumens 302, 304, 306, 308 and 310, each carrying a corresponding conductor 312, 314, 316, 318 and 320. A single, centrally located compression lumen 322 is provided. Like the configuration illustrated in FIGS. 2 and 3, the minimum wall thickness separating the conductor lumens from one another is greater than the minimum wall thickness separating the conductor lumens from the compression lumen. The compression lumen 322 is provided with the greatest radial dimension consistent with providing with providing a minimum wall thickness between the compression lumen and adjacent conductor lumens, and has its center located along a diameter passing through the centers of each of the various conductor lumens.

FIG. 5 illustrates an alternative embodiment corresponding more generally to that illustrated in FIG. 2. In FIG. 5, a conductor body 400 is provided with five conductor lumens 402, 404, 406, 408 and 410, and is provided with five, corresponding conductors 412, 414, 416, 418 and 420 and five compression lumens 422, 424, 426, 428 and 430 as in the embodiment illustrated in FIG. 2, each of the compression lumens has its center located along a diameter passing through the center of a corresponding conductor lumen, and the minimum wall thicknesses separating the compression lumens from the conductor lumens are less than the minimum wall thickness separating the conductor lumens from one another. In this view, the compression lumens display an elongated, egg-shaped cross-section, similar to that illustrated for the compression lumens in FIG. 2, in order to allow the compression lumens to display the maximum radial dimension consistent with provision of a desired minimum wall thickness between the compression lumens and adjacent conductor lumens. The lead of FIG. 5 is also provided with a central lumen 432, which may be employed as a conductor lumen, a stylet lumen a compression lumen or a through-lumen.

While the above invention is disclosed in the context of an implantable defibrillation lead, and in the context of a specific set of conductors, passing through the lead body, it should be recognized that the invention is believed to be generally applicable to all forms of multi-conductor medical electrical leads employing multi-lumen lead bodies. As such, the embodiments illustrated above should be considered exemplary, rather than limiting with regard to the claims that follow in conjunction with the above disclosure, we claim:

1. In a medical electrical lead having a plurality of elongated conductors located within an elongated lead body and provided with means for coupling proximal ends of said elongated conductors to an electrical medical device, the improvement wherein said lead body comprises a multi-lumen tube having a plurality of conductor lumens each containing a said elongated conductor, said conductor lumens spaced from one another by a first, minimum spacing and wherein said lead body further comprises a plurality of compression, lumens not containing a conductor and located intermediate at least two of said conductor lumens and spaced from said at least two conductor lumens by a second, minimal spacing of less then said first minimum spacing, one compression lumen being provided for each conductor lumen and located in said lead body diametrically opposite from one of said conductor lumens.

2. In a medical electrical lead having a plurality of elongated conductors located within a elongated insulative lead body and provided with means for coupling proximal ends of said elongated conductor to an electrical medical device, the improvement wherein said lead body comprises a multi-lumen tube having a plurality of conductor lumens, each containing a said elongated conductor, and a plurality of compression lumens not containing a conductor and having a center located such that each conductor lumen is located along a diameter of said lead body passing through a center of a said compression lumen, one compression lumen being provided for each conductor lumen and located in said lead body diametrically opposite from one of said conductor lumens.

3. In a medical electrical lead having a plurality of elongated conductors located within an elongated lead body and provided with means for coupling proximal ends of said elongated conductors to an electrical medical device, the improvement wherein said lead body comprises a multi-lumen tube having a plurality of conductor lumens each containing a said elongated conductor, said conductor lumens spaced from one another by a first minimum spacing and wherein said lead body further comprises at least one compression lumen, not containing a conductor and located intermediate at least two of said conductor lumens and spaced from said at least two conductor lumens by a second, minimal spacing of less than said minimal spacing, wherein at least one said compression lumen is tear drop shaped in cross section.

4. In a medical electrical lead having a plurality of elongated conductors located within an elongated lead body and provided with means for coupling proximal ends of said elongated conductors to an electrical medical device, the improvement wherein said lead body comprises a multi-lumen tube having three conductor lumens each containing a said elongated conductor, said conductor lumens spaced from one another by a first, minimum spacing and wherein said lead body further comprises three compression lumens each not containing a conductor and each located intermediate at least two of said conductor lumens and spaced from said at least two conductor lumens by a second, minimal spacing of less than said minimal spacing.

5. In a medical electrical lead having a plurality of elongated conductors located within an elongated insulative lead body and provided with means for coupling proximal ends of said elongated conductors to an electrical medical device, the improvement wherein said lead body comprises a multi-lumen tube having a plurality of conductor lumens, each containing a said elongated conductor and at least one compression lumen, not containing a conductor and having a center located such that each conductor lumen is located along a diameter of said lead body passing through a center of said at least one compression lumen, wherein said at least one compression lumen is tear drop shaped in cross section.

6. In a medical electrical lead having a plurality of elongated conductors located within an elongated lead body and provided with means for coupling proximal ends of said elongated conductors to an electrical medical device, the improvement wherein said lead body comprises a multi-lumen tube having a plurality of conductor lumens each containing a said elongated conductor and a plurality of compression lumens, one compression lumen being provided for each conductor lumen and located in said lead body diametrically opposite from one of said conductor lumens.

7. In a medical electrical lead having a plurality of elongated conductors located within said insulative lead body and provided with means for coupling proximal ends of said elongated conductors to an electrical medical device, the improvement wherein said lead body comprises a multi-lumen tube having a plurality of conductor lumens each containing said elongated conductor and a corresponding plurality of compression lumens each located intermediate two of said conductor lumens.

8. In a medical electrical lead having a plurality of elongated conductors located within an elongated insulative lead body and provided with means for coupling proximal ends of said elongated conductors to an electrical medical device, the improvement wherein said lead body comprises a multi-lumen tube having a plurality of conductor lumens each containing a said elongated conductor and at least one compression lumen not containing a conductor and having a center located such that said at least one compression lumen is located along a diameter of said lead body passing through a center of only one of said conductor lumens.

9. A lead according to claim 8, wherein a compression lumen is provided for each conductor lumen, located intermediate two of said conductor lumens.

10. A lead according to claim 8, wherein said lead body comprises a plurality of compression lumens, one compression lumen being provided for each conductor lumen and located in said lead body diametrically opposite from one of said conductor lumens.

11. A lead according to claim 8 or claim 9 or claim 10 wherein one of said compression lumens comprises a lumen located along a central axis of said lead body, intermediate said conductor lumens.

12. In a medical electrical lead having a plurality of elongated conductors located within an elongated lead body and provided with means for coupling proximal ends of said elongated conductors to an electrical medical device, the improvement wherein said lead body comprises a multi-lumen tube having a plurality of conductor lumens each containing a said elongated conductor and at least one compression lumen, not containing a conductor and located intermediate two of said conductor lumens, wherein said compression lumen is tear drop shaped in cross section.

13. A lead according to claim 12 wherein said lead body comprises a plurality of compression lumens, each located intermediate two of said conductor lumens.

14. A lead according to claim 12 wherein said lead body comprises a plurality of compression lumens, one compression lumen being provided for each conductor lumen and located in said lead body diametrically opposite from one of said conductor lumens.

* * * * *